(12) United States Patent
Bighetti

(10) Patent No.: US 8,588,918 B2
(45) Date of Patent: Nov. 19, 2013

(54) ASSEMBLY ARRANGEMENT FOR BANDAGE HOLDING A TRANSCUTANEOUS ELECTRICAL NERVE STIMULATION DEVICE

(75) Inventor: Moacyr Ramos Bighetti, Botucatu (BR)

(73) Assignee: Medecell do Brasil Comercio e Importacao LTDA, Sao Paulo (BR)

( * ) Notice: Subject to any disclaimer, the term of this patent is extended or adjusted under 35 U.S.C. 154(b) by 295 days.

(21) Appl. No.: 12/815,972

(22) Filed: Jun. 15, 2010

(65) Prior Publication Data

US 2010/0318168 A1 Dec. 16, 2010

(30) Foreign Application Priority Data

Jun. 15, 2009 (BR) .................................. 8901002 U

(51) Int. Cl.
*A61N 1/18* (2006.01)
*G09B 23/28* (2006.01)

(52) U.S. Cl.
USPC .............................. 607/46; 607/149; 434/262

(58) Field of Classification Search
USPC .................................. 607/46, 149, 2; 434/262
See application file for complete search history.

(56) References Cited

U.S. PATENT DOCUMENTS

2005/0181341 A1* 8/2005 Ewing et al. ................... 434/262
2006/0217786 A1* 9/2006 Shah ............................... 607/66

FOREIGN PATENT DOCUMENTS

| WO | WO 01-03768 A1 | 1/2001 |
| WO | WO 02-089911 A1 | 11/2002 |
| WO | WO 2006-113801 A2 | 10/2006 |

OTHER PUBLICATIONS

Johnson, "Transcutaneous electrical nerve stimulation (TENS)," in *Electrotherapy: Evidence-based Practice*, Chapter 16, pp. 253-296 (Elsevier Health Sciences, Apr. 2008).

* cited by examiner

*Primary Examiner* — Allen Porter, Jr.
(74) *Attorney, Agent, or Firm* — Leydig, Voit & Mayer, Ltd.

(57) ABSTRACT

The present utility model relates to the assembly arrangement for a bandage holding a portable small-scale transcutaneous electrical nerve stimulator device.

12 Claims, 2 Drawing Sheets

ASSEMBLY ARRANGEMENT FOR BANDAGE HOLDING A TRANSCUTANEOUS ELECTRICAL NERVE STIMULATION DEVICE

FIELD OF THE INVENTION

The invention relates to the assembly arrangement for a bandage holding a transcutaneous electrical nerve stimulator device which uses technology known as TENS, or "transcutaneous electric nerve stimulator."

In particular, it refers to a bandage of this type that is portable, disposable and small scale.

BACKGROUND OF THE INVENTION

Electrical stimulation of transcutaneous nerves is a simple and noninvasive analgesic technique. There are several known uses of this technique, including symptomatic management of acute non-malignant chronic pain. Reports in the technical literature state that use of this type of stimulation would also have antiemetic and healing effects.

Specifically, stimulation takes place by generating of current in a pulse generator which is applied between two areas of skin through contact points known as electrodes. As technical individuals will know, effective electrical stimulation must be comfortable, but strong enough to generate paraesthesia in the area of pain using frequencies of 1-250 pulses per second, and pulse duration of 50-1,000 micro seconds.

A reference publication on the subject of stimulation is the book Electrotherapy: Evidence-based Practice, Elsevier Health Sciences, editor: Tim Watson, chapter 16 by Mark Johnson "Transcutaneous electrical nerve stimulation (TENS)", p. 253-296, April 2008.

Bandages using TENS devices are known to the state of the art.

Some of the known devices are not portable, i.e. are assembled in such a way that electrodes placed on the patient's body are connected to large-scale electronic control modules. These units are for use when a patient is taken to a place where the electrical stimulation equipment is available, or may be placed in belts or other means to enable a patient to carry them with wires connecting to the area to be treated.

In light of this situation, in order to facilitate use without the need to move the patient to the place where the equipment is available, portable models have developed to be used by a patient anywhere. Some examples may be seen in the documents for patents WO02089911 and WO0103768, and WO2006/113801.

BRIEF SUMMARY OF THE INVENTION

Although the solutions found in the state of the art are technically suitable for use given their portability, there is also a need for disposable products with a simple and non-intimidating appearance whose use is intuitive for users so that they do not have to cope with complex equipment, and in particular it is safe and efficient because it avoids the use of very low levels of current (which are ineffective) or high ones (capable of causing the patient discomfort or pain) and that can also be reused or thrown away.

An advantage of the shape of the bandage on this invention is that it will ergonomically fit in with any part of the body, enabling electrodes to make contact with the skin of the user with an appropriate distance between them to ensure a flow of current beneficial for treating pain at low, medium or high intensity, under full control of the user.

Another advantage is that the thickness and dimensions and proportions of the components of the bandage are small enough for it to be used under a patient's clothing, in a totally discreet manner, without drawing attention.

Another highlight of this invention is the arrangement of buttons for controlling the TENS device associated with the bandage, which means that their functioning is immediately understood and usage is safe right from the start.

Therefore this design is an innovation in relation to the assembly arrangement for a bandage holding a transcutaneous electrical nerve stimulator device, and is characterized by comprising an elongated strip with:
 a central module fitted with a dashboard controlling electric current flowing between the two electrodes;
 two side tabs on the central module, opposite each other, each of said tabs being associated with one of said electrodes, for the purpose of making contact with the user's body.
 said dashboard with four buttons and an LED;
 said LED for the purpose of indicating that said device is operational when the light is on;
 one said button operational for the purpose of switching said device on or off;
 the remaining three buttons operational for individually controlling the level of current flowing between said electrodes.

The central module—and this is not decisive for this invention—comprises one or more electronic circuits and a battery providing power for the functioning of the TENS device.

As a particular feature, the central module side tabs have rounded and more ergonomic ends. In this respect, also as a particular feature, the electrodes are circular in shape and are located near the ends of the central module's side tabs.

These tabs may be composed of any laminated structural material, typically non-woven, an aspect that bears no relation to this invention. This material extends from the end of one tab to the end of the opposite tab, around the central module.

Also as a particular feature, each of the electrodes on each side of the central module's side tabs is coated with a layer of gel, which allows current to flow and promotes sufficient adhesion of the bandage to the skin of the user.

Also as a particular feature, each of these layers of gel is protected by a removable protective sheet before using the bandage.

Also as a particular feature, the dashboard is fitted with three buttons to control the level of current, corresponding to low, medium and high current respectively.

Also as a particular feature, these three buttons for individual control of the current being applied to the skin of the user are aligned and arranged in logical order of weak, medium and strong current, or in the order strong, medium and weak.

Also as a particular feature, the On/Off button may be associated with the function of switching the nature of the current used between steady and pulsed by holding the button down for a longer period, e.g. 3 seconds. If current is pulsed, the LED may indicate this fact by blinking.

A particular ratio between length and width of the bandage is 3:1, and the length is divided into three segments of lengths of the same order of magnitude, i.e. the central segment holding the central module, and the end segments comprising the side tabs. As a particular feature, the central module is slightly narrower than the side tabs.

Also as a particular feature, the length-to-width ratio of the side tabs is 1:1.

Also as a particular feature, the length of the bandage is about 15 cm.

Also as a particular feature, the format of the central module is quadrilateral, while the side tabs have one side in common with a side of the quadrilateral containing the central module, one side with rounded end opposite to the latter, and these two opposite sides are connected by two opposite parallel sides.

EXAMPLE

An example of practical embodiment of this invention is shown below, with dimensions and proportions that do not necessarily correspond to a real product, since the intention here to instructively illustrate and explain the different aspects of this invention. This embodiment is illustrative and does not impose any additional limitations beyond those expressed in the appended claims.

DETAILED DESCRIPTION OF AN EMBODIMENT

The figures show the assembly arrangement for a bandage using the present invention.

Figure 1:
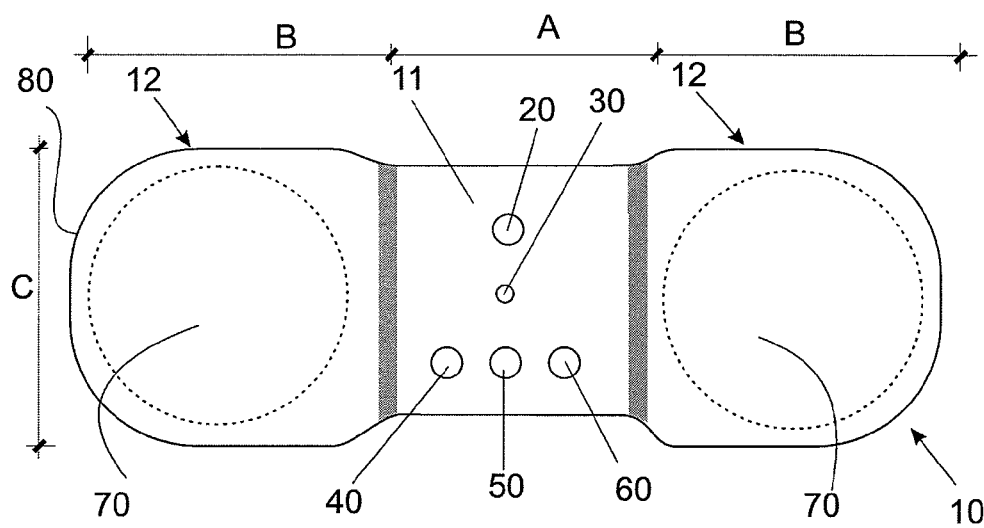
FIG. 1—upper view of bandage,
FIG. 2A—lower view of bandage with removable protective sheets still in place,
FIG. 2B—cross section view of bandage,
FIG. 3—lower view of bandage with removable protective sheets now removed.

Specifically in relation to FIG. 1 the illustration shows a bandage 10 comprising a central module 11, the length of which is A, fitted with side tabs 12 of length B. The width of these side tabs 12 is C and rounded ends 80.

The central module 11 (which houses the circuitry and battery of the TENS device, not illustrated) is slightly narrower than C, and is fitted with buttons 20, 40, 50, 60, and the LED 30. The button 20 switches the dashboard on or off (optionally it may also be used to toggle electrical current between constant and pulsed, if pressed for a longer period of e.g. 3 seconds), the LED 20 lights when the TENS device is working, the buttons 40, 50 and 60, illustrated with the letters L, M and H ("low", "medium" and "high") control current levels low, medium and high respectively.

Dotted lines in FIG. 1 show the outline of the electrodes 70, which are circular shaped in this embodiment. The dotted lines do not exist in the actual product and are intended to indicate for instructional purposes that the electrodes are located on the side opposite to the one illustrated here, as shown in detail in FIG. 3.

Figure 2A:
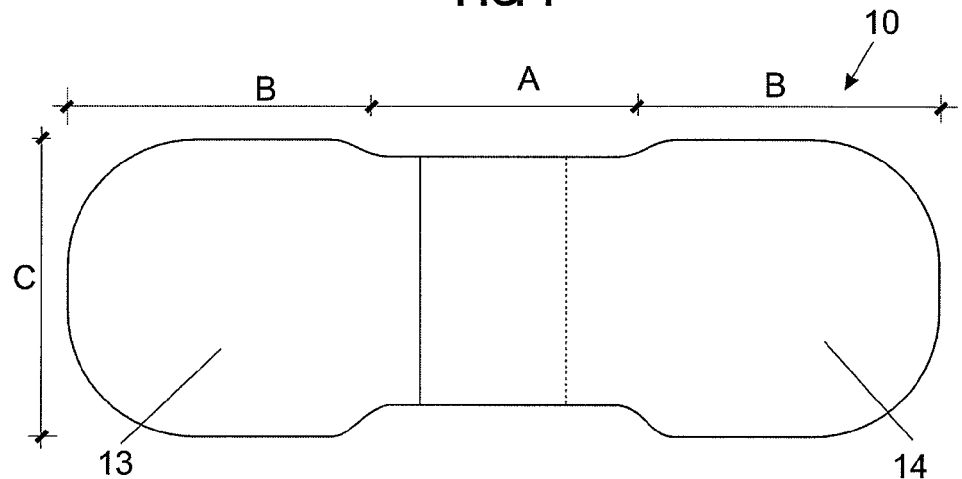
Figure 2B:
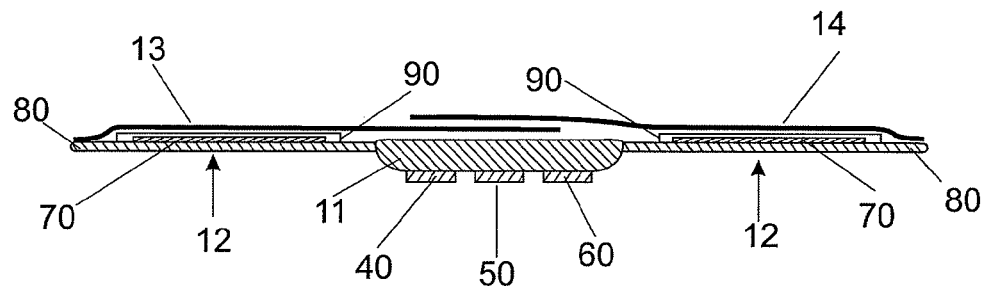
Figure 3:
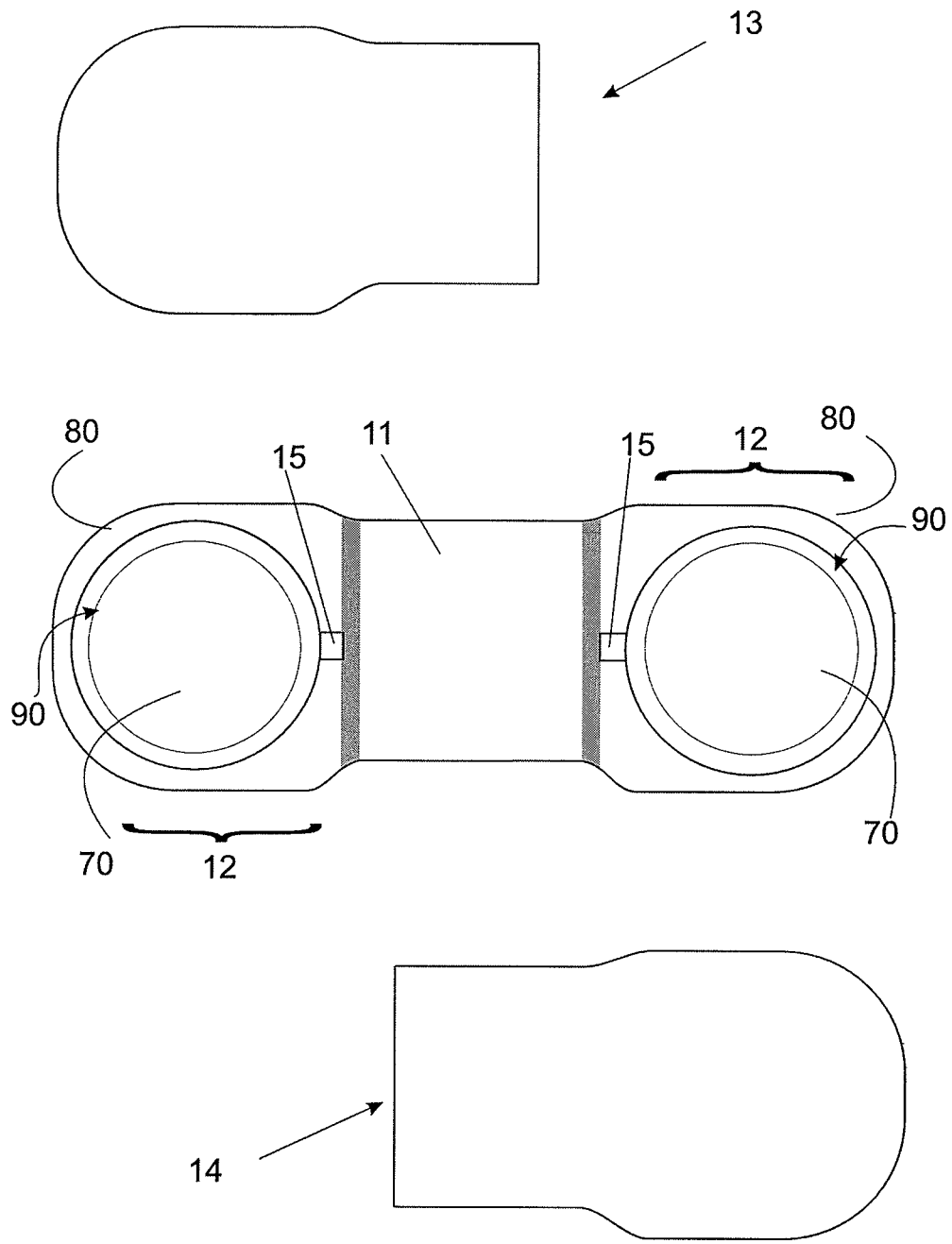

On the rear surface, shown in FIGS. 2A and 2B, the bandage 10, before use, is fitted with removable sheets 13 and 14 to protect the gel layer 90 around the electrodes 70. FIG. 3 shows these removable sheets 13 and 14 now removed from the rear surface of the bandage 10, showing the gel layer 90 covering the electrodes 70 and making contact with the patient's body on using the product.

The electrodes 70 are electrically connected to the dashboard by electrical connectors 15.

In this specific embodiment, the distance from the end of one side tab 12 to the end of the opposite side tab is 15.2 cm, corresponding to the sum of B+A+B, and B is just over 5 cm and A is just under 5 cm. C is 5.2 cm, while the width of the central module 11 is 4 cm. The thickness of the central module 11 is 0.7 cm, while the thickness of the side tabs 12, including electrodes 70 and gel layer 90 is 0.3 cm.

Let us repeat that the example described is only one particular embodiment of the assembly arrangement of the invention for a bandage holding a transcutaneous electrical nerve stimulator device. Those skilled in the art will know that there are other possible embodiments given the description provided, and these are also protected by the appended claims.

The invention claimed is:

1. Assembly arrangement for an elongated bandage holding a transcutaneous electrical nerve stimulation device on a user's body comprising:
    (a) a central module fitted with a dashboard controlling electric current between two electrodes;
    (b) two side tabs on the central module, opposite each other, each of said tabs being associated with one of said electrodes, adapted to contact the user's body;
    (c) said dashboard consisting of four buttons and an LED, said LED indicating that said device is operational when the light is on; one said button being an on/off button operational for switching said device on or off; the other three buttons operational for individually controlling the level of current between said electrodes at three respective predetermined levels of intensity of stimulation, including a low level button operational for supplying a low level of current between the electrodes when the on/off button is on, thereby providing a low level of intensity of stimulation, a medium level button operational for supplying a medium level of current between the electrodes when the on/off button is on, thereby providing a medium level of intensity of stimulation, and a high level button operational for supplying a high level of current between the electrodes when the on/off button is on, thereby providing a high level of intensity of stimulation.

2. Assembly arrangement for a bandage holding a transcutaneous electrical nerve stimulation device as per claim 1, wherein said tabs have rounded ends.

3. Assembly arrangement for a bandage holding a transcutaneous electrical nerve stimulation device as per claim 1, wherein the electrodes are of a circular shape.

4. Assembly arrangement for a bandage holding a transcutaneous electrical nerve stimulation device as per claim 1, wherein each of the electrodes is coated with a layer of gel.

5. Assembly arrangement for a bandage holding a transcutaneous electrical nerve stimulation device as per claim 4, wherein before use said layers of gel are protected by removable protective sheets.

6. Assembly arrangement for a bandage holding a transcutaneous electrical nerve stimulation device as per claim 4, wherein the central module has a thickness of around 0.7 cm, and each of the side tabs, electrodes and gel layers have a total thickness of around 0.3 cm.

7. Assembly arrangement for a bandage holding a transcutaneous electrical nerve stimulation device as per claim 1, wherein these three buttons are aligned.

8. Assembly arrangement for a bandage holding a transcutaneous electrical nerve stimulation device as per claim 1, wherein the on/off button, the LED and one of the buttons for controlling the level of current are aligned, and the three buttons for controlling current level are aligned.

9. Assembly arrangement for a bandage holding a transcutaneous electrical nerve stimulation device as per claim 1, wherein the bandage has a 3:1 length-to-width ratio.

10. Assembly arrangement for a bandage holding a transcutaneous electrical nerve stimulation device as per claim 1, wherein the central module and the side tabs each have a length, the lengths being of the same order of magnitude.

11. Assembly arrangement for a bandage holding a transcutaneous electrical nerve stimulation device as per claim 1, wherein a length-to-width ratio of the side tabs of 1:1.

12. Assembly arrangement for a bandage holding a transcutaneous electrical nerve stimulation device as per claim 1, wherein the central module has a length, the side tabs each have a length, and the bandage has a length and a width, wherein the bandage length is around 15 cm, the length of the central module and side tabs are each around 5 cm, and the width of said bandage is around 5 cm.

* * * * *